United States Patent [19]
Goldberg et al.

[11] Patent Number: 4,923,818
[45] Date of Patent: May 8, 1990

[54] DNA CLONE OF HUMAN TYPE IV COLLAGENASE

[75] Inventors: Gregory I. Goldberg; Arthur Z. Eisen, both of St. Louis, Mo.

[73] Assignee: Washington University, St. Louis, Mo.

[21] Appl. No.: 352,069

[22] Filed: May 15, 1989

Related U.S. Application Data

[63] Continuation-in-part of Ser. No. 93,421, Sep. 4, 1987.

[51] Int. Cl.5 .......................... C12N 1/00; C12N 9/64; C12N 15/00; C07H 21/00
[52] U.S. Cl. ..................................... 435/320; 435/226; 935/14; 536/27
[58] Field of Search ............... 435/219, 226, 235, 320; 536/27

[56] References Cited

U.S. PATENT DOCUMENTS 4,677,058 6/1987 Tryggvason ............................. 435/7
4,772,557 9/1988 Eisen et al. ........................... 435/320

FOREIGN PATENT DOCUMENTS 2142030 1/1985 United Kingdom ................ 435/226

OTHER PUBLICATIONS

Garbisa, S. et al, *J. Biol Chem*, vol. 261, pp. 2369–2375, Feb. 1986.
Seltzer et al., J. Biol. Chem. 256, 4662–4668 (1981).
Sopata, Biochim. Biophys. Acta 717, 26–31 (1982).
Seltzer et al., J. Chromatog. 326, 147–155 (1985).
Murphy et al., Biochim. Biophys. Acta 831, 49–58 (1985).
Hibbs et al., J. Biol. Chem. 260, 2493–2500 (1985).
Goldberg et al., J. Biol. Chem. 261, 6600–6605 (1986).
Yoakum et al., Science 227, 1174–1179 (1985).
Wilhelm et al., Proc. Natl. Acad. Sci. USA 84, 6725–6729 (1987).

*Primary Examiner*—Jayme A. Huleatt
*Attorney, Agent, or Firm*—Scott J. Meyer; James W. Williams, Jr.

[57] ABSTRACT

The cDNA clone representing the full size human type IV collagenase (gelatinase) is disclosed.

5 Claims, 14 Drawing Sheets

```
          10        20        30        40        50
GCATCTGGGCTTTAAACATACAAAGGGATTGCCAGGACCTGCGGCGGCG 60        70        80        90       100
GCGGCGGCGGCGGGGGCTGGCGCGGGGGCCGGACCATGAGCCGCTGAGC 110       120       130       140       150
CGGGCAAACCCCAGGCCACCGAGCCAGCGGACCCTCGGAGCAGCCCTGCG 160       170       180       190       200
CCGCGGAGCAGGCTCCAACCAGGCGGCGACGCGGCCACACGCACCGAGCC 210       220       230       240       250
AGCGACCCCCGGGCGACGCGCGGGGCCAGGGAGCGCTACGATGGAGGCGC
                                              M E A
         260       270       280       290       300
TAATGGCCCGGGGCGCGCTCACGGGTCCCCTGAGGGCGCTCTGTCTCCTG
 L M A R G A L T G P L R A L C L L
         310       320       330       340       350
GGCTGCCTGCTGAGCCACGCCGCCGCCGCCGCCGTCGCCCCATCATCAAGTT
 G C L L S N A A A A P S P I I K F
         360       370       380       390       400
CCCCGGCGATGTCGCCCCCAAAACGGACAAAGAGTTGGCAGTGCAATACC
 P G D V A P K T D K E L A V Q Y
         410       420       430       440       450
TGAACACCTTCTATGGCTGCCCCAAGGAGAGCTGCAACCTGTTTGTGCTG
 L N T F Y G C P K E S C N L F V L
         460       470       480       490       500
AAGGACACACTAAAGAAGATGCAGAAGTTCTTTGGACTGCCCCAGACAGG
 K D T L K K M Q K F F G L P Q T G
         510       520       530       540       550
TGATCTTGACCAGAATACCATCGAGACCATGCGGAAGCCACGCTGCGGCA
 D L D Q N T I E T M R K P R C G
         560       570       580       590       600
ACCCAGATGTGGCCAACTACAACTTCTTCCCTCGCAAGCCCAAGTGGGAC
 N P D V A N Y N F F P R K P K W D
         610       620       630       640       650
AAGAACCAGATCACATACAGGATCATCGGCTACACACCTGATCTGGACCC
 K N Q I T Y R I I G Y T P D L D P
         660       670       680       690       700
AGAGACAGTGGATGATGCCTTTGCTCGTGCCTTCCAAGTCTGGAGCGATG
 E T V D D A F A R A F Q V W S D
```

```
         710       720       730       740       750
TGACCCCACTGCGGTTTTCTCGAATCCATGATGGAGAGGCAGACATCATG
 V T P L R F S R I H D G E A D I M
         760       770       780       790       800
ATCAACTTTGGCCGCTGGGAGCATGGCGATGGATACCCCTTTGACGGTAA
 I N F G R W E N G D G Y P F D G K
         810       820       830       840       850
GGACGGACTCCTGGCTCATGCCTTCGCCCCAGGCACTGGTGTTGGGGGAG
 D G L L A N A F A P G T G V G G
         860       870       880       890       900
ACTCCCATTTTGATGACGATGAGCTATGGACCTTGGGAGAAGGCCAAGTG
 D S N F D D D E L W T L G E G Q V
         910       920       930       940       950
GTCCGTGTGAAGTATGGGAACGCCGATGGGGAGTACTGCAAGTTCCCCTT
 V R V K Y G N A D G E Y C K F P F
         960       970       980       990      1000
CTTGTTCAATGGCAAGGAGTACAACAGCTGCACTGATACTGGCCGCAGCG
 L F N G K E Y N S C T D T G R S
        1010      1020      1030      1040      1050
ATGGCTTCCTCTGGTGCTCCACCACCTACAACTTTGAGAAGGATGGCAAG
 D G F L W C S T T Y N F E K D G K
        1060      1070      1080      1090      1100
TACGGCTTCTGTCCCCATGAAGCCCTGTTCACCATGGGCGGCAACGCTGA
 Y G F C P N E A L F T M G G N A E
        1110      1120      1130      1140      1150
AGGACAGCCCTGCAAGTTTCCATTCCGCTTCCAGGGCACATCCTATGACA
 G Q P C K F P F R F Q G T S Y D
        1160      1170      1180      1190      1200
GCTGCACCACTGAGGGCCGCACGGATGGCTACCGCTGGTGCGGCACCACT
 S C T T E G R T D G Y R W C G T T
        1210      1220      1230      1240      1250
GAGGACTACGACCGCGACAAGAAGTATGGCTTCTGCCCTGAGACCGCCAT
 E D Y D R D K K Y G F C P E T A M
        1260      1270      1280      1290      1300
GTCCACTGTTGGTGGGAACTCAGAAGGTGCCCCCTGTGTCTTCCCCTTCA
 S T V G G N S E G A P C V F P F
        1310      1320      1330      1340      1350
CTTTCCTGGGCAACAAATATGAGAGCTGCACCAGCGCCGGCCGCAGTGAC
 T F L G N K Y E S C T S A G R S D
```

```
CCTCTGTCTCCTGGGCTGCCTGCTGAGCCACGCCGCCGCCGCGCCGTCGC        50
                                           A  P  S
CCATCATCAAGTTCCCCGGCGATGTCGCCCCCAAAACGGACAAAGAGTTG       100
 P  I  I  K  F  P  G  D  V  A  P  K  T  D  K  E  L
GCAGTGCAATACCTGAACACCTTCTATGGCTGCCCCAAGGAGAGCTGCAA       150
 A  V  Q  Y  L  N  T  F  Y  G  C  P  K  E  S  C  N
CCTGTTTGTGCTGAAGGACACACTAAAGAAGATGCAGAAGTTCTTTGGAC       200
 L  F  V  L  K  D  T  L  K  K  M  Q  K  F  F  G
TGCCCCAGACAGGTGATCTTGACCAGAATACCATCGAGACCATGCGGAAG       250
 L  P  Q  T  G  D  L  D  Q  N  T  I  E  T  M  R  K
CCACGCTGCGGCAACCCAGATGTGGCCAACTACAACTTCTTCCCTCGCAA       300
 P  R  C  G  N  P  D  V  A  N  Y  N  F  F  P  R  K
GCCCAAGTGGGACAAGAACCAGATCACATACAGGATCATCGGCTACACAC       350
  P  K  W  D  K  N  Q  I  T  Y  R  I  I  G  Y  T
CTGATCTGGACCCAGAGACAGTGGATGATGCCTTTACTCGTGCCTTCCAA       400
 P  D  L  D  P  E  T  V  D  D  A  F  A  R  A  F  Q
GTCTGGAGCGATGTGACCCCACTGCGGTTTTCTCGAATCCATGATGGAGA       450
 V  W  S  D  V  T  P  L  R  F  S  R  I  H  D  G  E
GGCAGACATCATGATCAACTTTGGCCGCTGGGAGCATGGCGATGGATACC       500
 A  D  I  M  I  N  F  G  R  W  E  H  G  D  G  Y
CCTTTGACGGTAAGGACGGACTCCTGGCTCATGCCTTCGCCCCAGGCACT       550
 P  F  D  G  K  D  G  L  L  A  H  A  F  A  P  G  T
GGTGTTGGGGGAGACTCCCATTTTGATGACGATGAGCTATGGACCTTGGG       600
 G  V  G  G  D  S  H  F  D  D  D  E  L  W  T  L  G
AGAAGGCCAAGTGGTCCGTGTGAAGTATGGGAACGCCGATGGGGAGTACT       650
 E  G  Q  V  V  R  V  K  Y  G  N  A  D  G  E  Y
GCAAGTTCCCCTTCTTGTTCAATGGCAAGGAGTACAACAGCTGCACTGAT       700
 C  K  F  P  F  L  F  N  G  K  E  Y  N  S  C  T  D
ACTGGCCGCAGCGATGGCTTCCTCTGGTGCTCCACCACCTACAACTTTGA       750
 T  G  R  S  D  G  F  L  W  C  S  T  T  Y  N  F  E
GAAGGATGGCAAGTACGGCTTCTGTCCCCATGAAGCCCTGTTCACCATGG       800
 K  D  G  K  Y  G  F  C  P  H  E  A  L  F  T  M
GCGGCAACGCTGAAGGACAGCCCTGCAAGTTTCCATTCCGCTTCCAGGGC       850
 G  G  N  A  E  G  Q  P  C  K  P  P  F  R  F  Q  G
ACATCCTATGACAGCTGCACCACTGAGGGCCGCACGGATGGCTACCGCTG       900
 T  S  Y  D  S  C  T  T  E  G  R  T  D  G  Y  R  W
```

FIG. 3A

```
GTGCGGCACCACTGAGGACTACGACCGCGACAAGAAGTATGGCTTCTGCC    950
 C  G  T  T  E  D  Y  D  R  D  K  K  Y  G  F  C

CTGAGACCGCCATGTCCACTGTTGGTGGGAACTCAGAAGGTGCCCCCTGT    1000
P  E  T  A  M  S  T  V  G  G  N  S  E  G  A  P  C

GTCTTCCCCTTCACTTTCCTGGGCAACAAATATGAGAGCTGCACCAGCGC    1050
 V  F  P  F  T  F  L  G  N  K  Y  E  S  C  T  S  A

CGGCCGCAGTGACGGAAAGATGTGGTGTGCGACCACAGCCAACTACGATG    1100
  G  R  S  D  G  K  M  W  C  A  T  T  A  N  Y  D

ACGACCGCAAGTGGGGCTTCTGCCCTGACCAAGGGTACAGCCTGTTCCTC    1150
D  D  R  K  W  G  F  C  P  D  Q  G  Y  S  L  F  L

GTGGCAGCCCACGAGTTTGGCCACGCCATGGGGCTGGAGCACTCCCAAGA    1200
 V  A  A  H  E  F  G  H  A  M  G  L  E  H  S  Q  D

CCCTGGGGCCCTGATGGCACCCATTTACACCTACACCAAGAACTTCCGTC    1250
  P  G  A  L  M  A  P  I  Y  T  Y  T  K  N  F  R

TGTCCCAGGATGACATCAAGGGCATTCAGGAGCTCTATGGGGCCTCTCCT    1300
 L  S  Q  D  D  I  K  G  I  Q  E  L  Y  G  A  S  P

GACATTGACCTTGGCACCGGCCCCACCCCCACACTGGGCCCTGTCACTCC    1350
 D  I  D  L  G  T  G  P  T  P  T  L  G  P  V  T  P

TGAGATCTGCAAACAGGACATTGTATTTGATGGCATCGCTCAGATCCGTG    1400
  E  I  C  K  Q  D  I  V  F  D  G  I  A  Q  I  R

GTGAGATCTTCTTCTTCAAGGACCGGTTCATTTGGCGGACTGTGACGCCA    1450
G  E  I  F  F  F  K  D  R  F  I  W  R  T  V  T  P

CGTGACAAGCCCATGGGGCCCCTGCTGGTGGCCACATTCTGGCCTGAGCT    1500
 R  D  K  P  M  G  P  L  L  V  A  T  F  W  P  E  L

CCCCGGAAAAGATTGATGCGGTATACGAGGCCCCACAGGAGGAGAAGGCTG    1550
  P  E  K  I  D  A  V  Y  E  A  P  Q  E  E  K  A

TGTTCTTTGCAGGGAATGAATACTGGATCTACTCAGCCAGCACCTTGGAG    1600
V  F  F  A  G  N  E  Y  W  I  Y  S  A  S  T  L  E

CGAGGGTACCCCAAGCCACTGACCAGCCTGGGACTGCCCCCTGATGTCCA    1650
 R  G  Y  P  K  P  L  T  S  L  G  L  P  P  D  V  Q

GCGAGTGGATGCCGCCTTTAACTGGAGCAAAAACAAGAAGACATACATCT    1700
  R  V  D  A  A  F  N  W  S  K  N  K  K  T  Y  I

TTGCTGGAGACAAATTCTGGAGATACAATGAGGTGAAGAAGAAAATGGAT    1750
F  A  G  D  K  F  W  R  Y  N  E  V  K  K  K  M  D

CCTGGCTTCCCCAAGCTCATCGCAGATGCCTGGAATGCCATCCCCGATAA    1800
 P  G  F  P  K  L  I  A  D  A  W  N  A  I  P  D  N
```

FIG. 3B

```
CCTGGATGCCGTCGTGGACCTGCAGGGCGGCGGTCACAGCTACTTCTTCA  1850
 L   D   A   V   V   D   L   Q   G   G   G   H   S   Y   F   F

AGGGTGCCTATTACCTGAAGCTGGAGAACCAAAGTCTGAAGAGCGTGAAG  1900
 K   G   A   Y   Y   L   K   L   E   N   Q   S   L   K   S   V   K

TTTGGAAGCATCAAATCCGACTGGCTAGGCTGCTGAGCTGGCCCTGGCTC  1950
 F   G   S   I   K   S   D   W   L   G   C   *

CCACAGGCCCTTCCTCTCCACTGCCTTCGATACACCGGGCCTGGAGAACT  2000

AGAGAAGGACCCGGAGGGGCCTGGCAGCCGTGCCTTCAGCTCTACAGCTA  2050

ATCAGCATTCTCACTCCTACCTGGTAATTTAAGATTCCAGAGAGTGGCTC  2100

CTCCCGGTGCCCAAGAATAGATGCTGACTGTACTCCTCCCAGGCGCCCCT  2150

TCCCCCTCCAATCCCACCAACCCTCAGAGCCACCCCTAAAGAGATACTTT  2200

GATATTTTCAACGCAGCCCTGCTTTGGGCTGCCCTGGTGCTGCCACACTT  2250

CAGGCTCTTCTCCTTTCACAACCTTCTGTGGCTCACAGAACCCTTGGAGC  2300

CAATGGAGACTGTCTCAAGAGGGCACTGGTGGCCCGACAGCCTGGCACAG  2350

GGCAGTGGGACAGGGCATGGCCAGGTGGCCACTCCAGACCCCTGGCTTTT  2400

CACTGCTGGCTGCCTTAGAACCTTTCTTACATTAGCAGTTTGCTTTGTAT  2450

GCACTTTGTTTTTTTCTTTGGGTCTTGTTTTTTTTTCCACTTAGAAATT  2500

GCATTTCCTGACAGAAGGACTCAGGTTGTCTGAAGTCACTGCACAGTGCA  2550

TCTCAGCCCACATAGTGATGGTTCCCCTGTTCACTCTACTTAGCATGTCC  2600

CTACCGAGTCTCTTCTCCACTGGATGGAGGAAAACCAAGCCGTGGCTTCC  2650

CGCTCAGCCCTCCCTGCCCCTCCCTTCAACCATTCCCCATGGGAAATGTC  2700

AACAAGTATGAATAAAAGACACCTACTGAGTGGC                 2733
```

FIG. 3C

```
A:
APSPIIKFPGDVAPKTDKELAVQ-YLNTFYGCPKESCNLFVL-KDT----    44
    ATLETQEQDVDL   K   EKY NLKNDGRQVEKR-RNSGPVV
    YPLD AARGEDTSMNL   K   ENYYDLK DVKQ-  RR   SGPVV
    SYPLHGSEEDAGM VLQK-  ENY  LE DVKQFTKK-  SSPVV

--LKK---MQKFFGLPQTGDLDQNTIETMRKPRCGNPDVANYNFFPRKPK    89
EK  ---Q   E    KV   KP AE LKV KQ       V    QFVLTEGN R
---  IRE    L   EV   K  SD L V         V   GHFRT   GI
---  IQE    L   KM   K  S  M L H       V   GGFST   GS

WDKNQITYRIIGYTPDLDPETVDDAFARAFQVWSDVTPLRFSRIHDGEAD   139
 EQTHLR   EN     PRAD  H IEK   L   N    T  TKVSE  Q
 R THL    VN     PKDA  S VEK  LK  EE    T    LYE
 R  H S   VN  L  PR S  S IE   LK  EE    T    SE

IMINFGRWEHGDGYPFDGKDGLLAHAFAPGTGVGGDSHFDDDELWTLGEG   189
    S V GD R NS    PG N       Q  P I   A    E   R  NNFR
    S AVR      F   PGNV       Y  P IN  A    Q    KDTT
    S AVE      FI  PGMV       Y  P TN  A    R    DDVT

QVVRVKYGNADGEYCKFPFLFNGKEYNSCTDTGRSDGFLWCSTTYNFEKD   239
EYN
GTN***********************************************
GTN

GKYGFCPHEALFTMGGNAEGQPCKFPFRFQGTSYDSCTTEGRTDGYRWCG   289
**************************************************
          QTY   LN E   VL   TYN RTFY      Q   HL  S    +

TTEDYDRDKKYGFCPETAMSTV-----GGNSEGAPCVFPFTFLGNKYESC   334
**************************************************
   SN EQ Q   S  TDH--- LVQTQ      N  L H    LYNNHN TD   +

TSAGRSDGKMWCATTANYDDDRKWGFCPDQGYSLFLVAAHEFGHAMGLEH   384
                                 HR       L   SL   S
*******************************  I       SL   F
                                           L  FL   F
    E  R NMKG     Q    A Q F    --------M     EICTTNEGV  +

SQDPGALMAPIYTYTKN---FR----LSQDDIKGIQELYGA---SPDIDLG   425
 T I      Y  S   FSGD---VQ---  A     D   AI   R--- QNPVQP
 ANTE     Y L HSLTDLTR  ---         N   S  PPPD   ET--P
 ANAE     Y V KSSTDLAR H---         VD  S   PPTE   VLVV
M                                                         +

TGPTPTLGPVT-PEICKQDIV------FDGIAQIRGEIFFFKDRFIWRTV-   469
I   Q-------- KA DSKLT-----   A TT     VM      YM  N-
LV  E----  -P PGTPANCDPALS   AVSTL     LI    HF KS-
----    KSNSLD TLPMCSSALS-- AVSTL      VL    HF KSL

-TPRDKPMGPLLVATFWPELPEKIDAVYEAPQEEKAVFFAGNEYWIYSAS   517
-PFYPEVELNFISV-   Q  NGLE A  FADRDEVR   K   K  AVQGQ
-LRKLE ELH ISS-   S  SGV A  VTSKDLVFI ELH   QF AIRGN
R   EPGFYL--ISS-  S  SNM A  VTNRDTVFILK     QI AIRGH

TLERGYPKPLTSLGLPPDVQRV-DAAFNWSKNKKTYIFAGDKFWRYNEVK   566
NVLH ·    DIY SFGF RTVKHI    LSEENTG    F VAN Y    D Y
EVRA    RGIHT  F   T RKI-    ISDKEKN    F VE  Y   FD KR
EELA    SIHT      ET KI-     ISLKDQ     F VE      FD K

KKMDPGFPKLIADAWNAIPDNLDAVVDLQGGGHSYFFKGAYYLKLENQSL   616
RS   SY   M   HDFPG  GHKV    FMKD FF--    H TRQY FDPKTK
NS  E·        EDFPG  DSKI    FEEF FF--    T SSQ--  FDPN
QS     E  RK  ENFPG  GTKV    FEAF FL--    S SSQ--  FDPN

KSVKFGSIKSD-WLGC*           GEL                      631
RILTLQKAN --  FN RKN*       COL
AKKVTHTL  NS *              STR
AGKVTHIL  NS FN *           TRA

B:
GNADGEYCKFPFLFNGKEYNSCTDTGRSDGFLWCSTTYNFEKDGKYGFCP
   E QP       R Q TS D     TE   T   YR  G   EDYDR K
   SE AP V      T L NK E    SA      KM  A   A YDD R W

HEA--LFTMG                                           254
ET MSTVG--                                           312
DQGYS  L--                                           370
```

EcoRI       EcoRI     DraI    BssHII
                     XmnI                  TS AUG    XmnI

—— 0.5 Kbp

FIG. 8B

```
CCAGATCGCTGAGAGAGGCAAGTGGGGTGACGAGGTCGTGCACTGAGGGTGGACGTAGAGG      -230
CCAGGAGTAGCAGGCGGCCCGGGGAAAAAGAGGTGGAGAAAAAGAGAGAAAAGTG           -170
GAGGAGGGCGAGTAGGGGGTGGGCAGAGAGGGCGGGCCCGAGTGCGCCCCCGCC            -110
CAGCCCCCCGTCTGCCAGCTCCCTCCCAGCCCTCGGCTACATCTGCCGCTCCCTCCCT         -50
TGTTTCCGCTGCATCCAGACTTCCTCAGGCGGTGCTGGAGGCTGCGCATCTGGGGCTTT        10
                                                        +1
AACATACAAAGGATTGCCAGGACCTGCGGCGGCTGCGGCGGCTGGGCGC                 70
GGGGCCGGACCATGAGCCGCTGAGCCGCCACCGAGCCAGCGACCC                     130
TCGGAGCAGCCCTGCGCCGGAGCTCCAACCAGGCGGACGCGGCCACACGCAC              190
CGAGCCAGCGACCCCCGGGCGACGCGCAGGGAGAGCGCTACGATGGAGGCGCTAAT          250
                                              MetGluAlaLeuMe
GGCCCGGGGGCGCGCTCACGGGTCCCCTGAGGGCGCTCTGTCTTCCTGGGCTGCCTGCTGAG     310
tAlaArgGlyAlaLeuThrGlyProLeuArgAlaLeuCysLeuLeuGlyCysLeuLeuSe
CCACGCCGCCGCCGCCGTCGCCCATCATCAAGTTCCCCGGCGATGTCGCCCCCAAAAC         370
rHisAlaAlaAlaAlaProSerProIleIleLysPheProGlyAspValAlaProLysTh
GGACAAAGAGTTGGCAGTGCAATACCTGAACACCTTCTAT                           410
rAspLysGluLeuAlaValGlnTyrLeuAsnThrPheTyr
```

```
           10         20         30         40         50
       GCATCTGGGGCTTTAAACATACAAAGGGATTGCCAGGACCTGCGGCGGCG 60         70         80         90        100
       GCGGCGGCGGCGGGGGCTGGGCGCGGGGGCCGGACCATGAGCCGCTGAGC 110        120        130        140        150
       CGGGCAAACCCCAGGCCACCGAGCCAGCGGACCCTCGGAGCAGCCCTGCG 160        170        180        190        200
       CCGCGGAGCAGGCTCCAACCAGGCGGCGACGCGGCCACACGCACCGAGCC 210        220        230        240        250
       AGCGACCCCCGGGCGACGCGCGGGGCCAGGGAGCGCTACGATGGAGGCGC
                                                      M  E  A 260        270        280        290        300
       TAATGGCCCCGGGGCGCGCTCACGGGTCCCCTGAGGGCGCTCTGTCTCCTG
       L  M  A  R  G  A  L  T  G  P  L  R  A  L  C  L  L 310        320        330        340        350
       GGCTGCCTGCTGAGCCACGCCGCCGCCGCGCCGTCGCCCATCATCAAGTT
        G  C  L  L  S  N  A  A  A  A  P  S  P  I  I  K  F 360        370        380        390        400
       CCCCCGGCGATGTCGCCCCCAAAACGGACAAAGAGTTGGCAGTGCAATACC
        P  G  D  V  A  P  K  T  D  K  E  L  A  V  Q  Y 410        420        430        440        450
       TGAACACCTTCTATGGCTGCCCCAAGGAGAGCTGCAACCTGTTTGTGCTG
       L  N  T  F  Y  G  C  P  K  E  S  C  N  L  F  V  L 460        470        480        490        500
       AAGGACACACTAAAGAAGATGCAGAAGTTCTTTGGACTGCCCCAGACAGG
        K  D  T  L  K  K  M  Q  K  F  F  G  L  P  Q  T  G 510        520        530        540        550
       TGATCTTGACCAGAATACCATCGAGACCATGCGGAAGCCACGCTGCGGCA
        D  L  D  Q  N  T  I  E  T  M  R  K  P  R  C  G 560        570        580        590        600
       ACCCAGATGTGGCCAACTACAACTTCTTCCCTCGCAAGCCCAAGTGGGAC
       N  P  D  V  A  N  T  N  F  F  P  R  K  P  K  W  D 610        620        630        640        650
       AAGAACCAGATCACATACAGGATCATCGGCTACACACCTGATCTGGACCC
        K  N  Q  I  T  Y  R  I  I  G  Y  T  P  D  L  D  P 660        670        680        690        700
       AGAGACAGTGGATGATGCCTTTGCTCGTGCCTTCCAAGTCTGGAGCGATG
        E  T  V  D  D  A  F  A  R  A  F  Q  V  W  S  D
```

FIG. 9A

```
       710        720        730        740        750
TGACCCCACTGCGGTTTTCTCGAATCCATGATGGAGAGGCAGACATCATG
 V  T  P  L  R  F  S  R  I  H  D  G  E  A  D  I  M 760        770        780        790        800
ATCAACTTTGGCCGCTGGGAGCATGGCGATGGATACCCCTTTGACGGTAA
 I  N  F  G  R  W  E  N  G  D  G  Y  P  F  D  G  K 810        820        830        840        850
GGACGGACTCCTGGCTCATGCCTTCGCCCCAGGCACTGGTGTTGGGGGAG
  D  G  L  L  A  N  A  F  A  P  G  T  G  V  G  G 860        870        880        890        900
ACTCCCATTTTGATGACGATGAGCTATGGACCTTGGGAGAAGGCCAAGTG
  D  S  N  F  D  D  D  E  L  W  T  L  G  E  G  Q  V 910        920        930        940        950
GTCCGTGTGAAGTATGGGAACGCCGATGGGGAGTACTGCAAGTTCCCCTT
 V  R  V  K  Y  G  N  A  D  G  E  Y  C  K  F  P  F 960        970        980        990       1000
CTTGTTCAATGGCAAGGAGTACAACAGCTGCACTGATACTGGCCGCAGCG
  L  F  N  G  K  E  Y  N  S  C  T  D  T  G  R  S 1010       1020       1030       1040       1050
ATGGCTTCCTCTGGTGCTCCACCACCTACAACTTTGAGAAGGATGGCAAG
 D  G  F  L  W  C  S  T  T  Y  N  F  E  K  D  G  K 1060       1070       1080       1090       1100
TACGGCTTCTGTCCCCATGAAGCCCTGTTCACCATGGGCGGCAACGCTGA
 Y  G  F  C  P  N  E  A  L  F  T  M  G  G  N  A  E 1110       1120       1130       1140       1150
AGGACAGCCCTGCAAGTTTCCATTCCGCTTCCAGGGCACATCCTATGACA
  G  Q  P  C  K  F  P  F  R  F  Q  G  T  S  Y  D 1160       1170       1180       1190       1200
GCTGCACCACTGAGGGCCGCACGGATGGCTACCGCTGGTGCGGCACCACT
 S  C  T  T  E  G  R  T  D  G  Y  R  W  C  G  T  T 1210       1220       1230       1240       1250
GAGGACTACGACCGCGACAAGAAGTATGGCTTCTGCCCTGAGACCGCCAT
 E  D  Y  D  R  D  K  K  Y  G  F  C  P  E  T  A  M 1260       1270       1280       1290       1300
GTCCACTGTTGGTGGGAACTCAGAAGGTGCCCCCTGTGTCTTCCCCTTCA
  S  T  V  G  G  N  S  E  G  A  P  C  V  F  P  F 1310       1320       1330       1340       1350
CTTTCCTGGGCAACAAATATGAGAGCTGCACCAGCGCCGGCCGCAGTGAC
  T  F  L  G  N  K  Y  E  S  C  T  S  A  G  R  S  D
```

FIG. 9B

```
          1360       1370       1380       1390       1400
GGAAAGATGTGGTGTGCGACCACAGCCAACTACGATGACGACCGCAAGTG
 G  K  M  W  C  A  T  T  A  N  Y  D  D  D  R  K  W 1410       1420       1430       1440       1450
GGGCTTCTGCCCTGACCAAGGGTACAGCCTGTTCCTCGTGGCAGCCCACG
 G  F  C  P  D  Q  G  Y  S  L  F  L  V  A  A  H 1460       1470       1480       1490       1500
AGTTTGGCCACGCCATGGGGCTGGAGCACTCCCAAGACCCTGGGGCCCTG
 E  F  G  H  A  M  G  L  E  H  S  Q  D  P  G  A  L 1510       1520       1530       1540       1550
ATGGCACCCATTTACACCTACACCAAGAACTTCCGTCTGTCCCAGGATGA
 M  A  P  I  Y  T  Y  T  K  N  F  R  L  S  Q  D  D 1560       1570       1580       1590       1600
CATCAAGGGCATTCAGGAGCTCTATGGGGCCTCTCCTGACATTGACCTTG
 I  K  G  I  Q  E  L  Y  G  A  S  P  D  I  D  L 1610       1620       1630       1640       1650
GCACCGGCCCCACCCCCACACTGGGCCCTGTCACTCCTGAGATCTGCAAA
 G  T  G  P  T  P  T  L  G  P  V  T  P  E  I  C  K 1660       1670       1680       1690       1700
CAGGACATTGTATTTGATGGCATCGCTCAGATCCGTGGTGAGATCTTCTT
 Q  D  I  V  F  D  G  I  A  Q  I  R  G  E  I  F  F 1710       1720       1730       1740       1750
CTTCAAGGACCGGTTCATTTGGCGGACTGTGACGCCACGTGACAAGCCCA
 F  K  D  R  F  I  W  R  T  V  T  P  R  D  K  P 1760       1770       1780       1790       1800
TGGGGCCCCTGCTGGTGGCCACATTCTGGCCTGAGCTCCCGGAAAAGATT
 M  G  P  L  L  V  A  T  F  W  P  E  L  P  E  K  I 1810       1820       1830       1840       1850
GATGCGGTATACGAGGCCCCACAGGAGGAGAAGGCTGTGTTCTTTGCAGG
 D  A  V  Y  E  A  P  Q  E  E  K  A  V  F  F  A  G 1860       1870       1880       1890       1900
GAATGAATACTGGATCTACTCAGCCAGCACCTTGGAGCGAGGGTACCCCA
 N  E  Y  W  I  Y  S  A  S  T  L  E  R  G  Y  P 1910       1920       1930       1940       1950
AGCCACTGACCAGCCTGGGACTGCCCCCTGATGTCCAGCGAGTGGATGCC
 E  P  L  T  S  L  G  L  P  P  D  V  Q  R  V  D  A 1960       1970       1980       1990       2000
GCCTTTAACTGGAGCAAAAACAAGAAGACATACATCTTTGCTGGAGACAA
 A  F  N  W  S  K  N  K  K  T  Y  I  F  A  G  D  K
```

FIG. 9C

```
      2010      2020      2030      2040      2050
ATTCTGGAGATACAATGAGGTGAAGAAGAAAATGGATCCTGGCTTCCCCA
  F  W  R  Y  N  E  V  K  K  K  M  D  P  G  F  P 2060      2070      2080      2090      2100
AGCTCATCGCAGATGCCTGGAATGCCATCCCCGATAACCTGGATGCCGTC
  K  L  I  A  D  A  W  N  A  I  P  D  N  L  D  A  V 2110      2120      2130      2140      2150
GTGGACCTGCAGGGCGGCGGTCACAGCTACTTCTTCAAGGGTGCCTATTA
  V  D  L  Q  G  G  G  H  S  Y  F  F  K  G  A  ⊥  Y 2160      2170      2180      2190      2200
CCTGAAGCTGGAGAACCAAAGTCTGAAGAGCGTGAAGTTTGGAAGCATCA
    L  K  L  E  N  Q  S  L  K  S  V  K  F  G  S  I 2210      2220      2230      2240      2250
AATCCGACTGGCTAGGCTGCTGAGCTGGCCCTGGCTCCCACAGGCCCTTC
  K  S  D  W  L  G  C  *

2260      2270      2280      2290      2300
CTCTCCACTGCCTTCGATACACCGGGCCTGGAGAACTAGAGAAGGACCCG 2310      2320      2330      2340      2350
GAGGGGCCTGGCAGCCGTGCCTTCAGCTCTACAGCTAATCAGCATTCTCA 2360      2370      2380      2390      2400
CTCCTACCTGGTAATTTAAGATTCCAGAGAGTGGCTCCTCCCGGTGCCCA 2410      2420      2430      2440      2450
AGAATAGATGCTGACTGTACTCCTCCCAGGCGCCCCTTCCCCCTCCAATC 2460      2470      2480      2490      2500
CCACCAACCCTCAGAGCCACCCCTAAAGAGATACTTTGATATTTTCAACG 2510      2520      2530      2540      2550
CAGCCCTGCTTTGGGCTGCCCTGGTGCTGCCACACTTCAGGCTCTTCTCC 2560      2570      2580      2590      2600
TTTCACAACCTTCTGTGGCTCACAGAACCCTTGGAGCCAATGGAGACTGT 2610      2620      2630      2640      2650
CTCAAGAGGGCACTGGTGGCCCGACAGCCTGGCACAGGGCAGTGGGACAG 2660      2670      2680      2690      2700
GGCATGGCCAGGTGGCCACTCCAGACCCCTGGCTTTTCACTGCTGGCTGC 2710      2720      2730      2740      2750
CTTAGAACCTTTCTTACATTAGCAGTTTGCTTTGTATGCACTTTGTTTTT 2760      2770      2780      2790      2800
TTCTTTGGGTCTTGTTTTTTTTTTCCACTTAGAAATTGCATTTCCTGACA
```

FIG. 9D

```
        2810      2820      2830      2840      2850
GAAGGACTCAGGTTGTCTGAAGTCACTGCACAGTGCATCTCAGCCCACAT 2860      2870      2880      2890      2900
AGTGATGGTTCCCCTGTTCACTCTACTTAGCATGTCCCTACCGAGTCTCT 2910      2920      2930      2940      2950
TCTCCACTGGATGGAGGAAAACCAAGCCGTGGCTTCCCGCTCAGCCCTCC 2960      2970      2980      2990      3000
CTGCCCCTCCCTTCAACCATTCCCCATGGGAAATGTCAACAAGTATGAAT 3010      3020
AAAGACACCTACTGAGTGGC
```

FIG. 9E

DNA CLONE OF HUMAN TYPE IV COLLAGENASE

CROSS-REFERENCE TO RELATED APPLICATION

This is a continuation-in-part of copending application Ser. No. 07/93,421, filed Sept, 4, 1987.

BACKGROUND OF THE INVENTION

This invention relates to type IV collagenase, hereinafter also referred to as gelatinase. More particularly, the invention relates to the cDNA clone representing the full size human type IV collagenase (gelatinase).

Collagens constitute the most abundant proteins of the extracellular matrix (ECM) in mammalian organisms. Collagen and other macromolecules of the ECM are deposited by resident cells and organized into a three-dimensional meshwork. This ECM environment plays an essential role in guiding cell migration, and in cell-to-cell communication during morphogenetic processes. The restructuring of the ECM during remodeling occurs as a cooperative multistep process involving a localized degradation of existing macromolecules, rearrangement of the cytoskeleton, cell translocation, and deposition of new ECM components.

The few secreted proteases capable of initiaing the degradation of ECM proteins previously identified include; fibroblast and granulocyte collagenases which degrade interstitial collagens, collagenase degrading type IV basement membrane collagen, stromelysin and gelatinase. Examination of the specific role of each protease in ECM metabolism is complicated by the difficulty of differential identification of the enzymes.

Type IV collagenase (gelatinase) represents a new member of an emerging gene family coding for secreted ECM metalloproteases. Initial identification, purification and/or partial characterization of this protease is described by Seltzer et al., *J. Biol. Chem.* 256, 4662–4668 (1981); Sopata, *Biochim. Biophys. Acta* 717, 26–31 (1982); Seltzer et al., *J. Chromatog.* 326, 147–155 (1985); Murphy et al., *Biochim. Biophys. Acta* 831, 49–58 (1985); and Hibbs et al., *J. Biol. Chem.* 260, 2493–2500 (1985).

Recent advances in biochemistry and in recombinant DNA technology have made it possible to synthesize specific proteins, for example, enzymes, under controlled conditions independent of the organism from which they are normally isolated. These biochemical synthetic methods employ enzymes and subcellular components of the protein synthesizing systems of living cells, either in vitro in cell-free systems, or in vivo in microorganisms. In either case, the principal element is provision of a deoxyribonucleic acid (DNA) of specific sequence which contains the information required to specify the desired amino acid sequence. Such a specific DNA sequence is termed a gene. The coding relationships whereby a deoxyribunucleotide sequence is used to specify the amino acid sequence of a protein is well-known and operates according to a fundamental set of principles. See, for example, Watson, *Molecular Biology of the Gene*, 3d ed., Benjamin-Cummings, Menlo Park, Calif., 1976.

A cloned gene may be used to specify the amino acid sequence of proteins synthesized by in vitro systems. RNA-directed protein synthesizing systems are well-established in the art. Doublestranded DNA can be induced to generate messenger RNA (mRNA) in vitro with subsequent high fidelity translation of the RNA sequence into protein.

It is now possible to isolate specific genes or portions thereof from higher organisms, such as man and animals, and to transfer the genes or fragments to microorganisms such as bacteria or yeasts. The transferred gene is replicated and propogated as the transformed microorganism replicates. Consequently, the transformed microorganism is endowed with the capacity to make the desired protein or gene which it encodes, for example, an enzyme, and then passes on this capability to its progeny. See, for example, Cohen and Boyer, U.S. Pat. Nos. 4,237,224 and 4,468,464.

BRIEF DESCRIPTION OF THE INVENTION

In accordance with the present invention, the cDNA clone representing the full size human type IV collagenase (gelatinase) has been developed. The clone, pGel 186.2, contains 2733 base pairs (bp) which represents the full gelatinase mRNA sequence with the exception of the leader sequence coding for the first few amino acids of the signal peptide.

The cDNA sequence has the coding capacity for the last 13 amino acids of the signal peptide and 631 amino acids of gelatinase protein ($M_r = 70,975$ daltons) followed by 750 bp long 3' untranslated region, including a putative poly A addition site.

The gelatinase protein sequence consists of three domains, an amino terminal domain, I, of 192 amino acids, a middle domain, II, of 175 amino acids, and a carboxy terminal domain, III, of 264 amino acids. The outer domains I and II show homology to collagenase described in U.S. Pat. No. 4,772,557, the disclosure of which is incorporated herein by reference, and to stromelysin described by Wilhelm et al., *Proc. Natl. Acad. Sci. USA*, 84, 6725–6729 (1987). The middle domain II, 175 amino acids long, is organized into three 58 amino acid long head-to-tail repeats which show homology to the type II motif of the collagen binding domain of fibronectin. In contrast to the expression of human fibroblast collagenase and stromelysin, the expression of type IV collagenase (gelatinase) by a variety of human fibroblast cell strains is not modulated by the tumor promoter TPA (12-0-tetradecanolphorbol 13-acetate).

The proenzyme is secreted in a single latent form with $M_r$ 72,000 and can be activated with p-aminophenylmercuric acid (APMA) to catalyze cleavage of ECM macromolecules. The substrates in their order of preference are: gelatin, type IV collagen, type V collagen, fibronectin and type VII collagen. The enzyme does not cleave interstitial collagens or laminin.

The original source of the protein material illustrated herein was H-ras transformed human bronchial epithelial cells (TBE-1). The culture and characterization of these cells is described by Yoakum et al., *Science* 227, 1174–1179 (1985). Suitable cells are also readily available from ordinary skin biopsies, and most normal adult human fibroblast cells can be used as source materials. Human fibroblasts from skin are also a source of the enzyme.

The human type IV collagenase (gelatinase) described herein has potential use in treatment of hypertrophic scars, keloids and intervertebral disc disease.

DETAILED DESCRIPTION OF THE INVENTION

Figure 1:
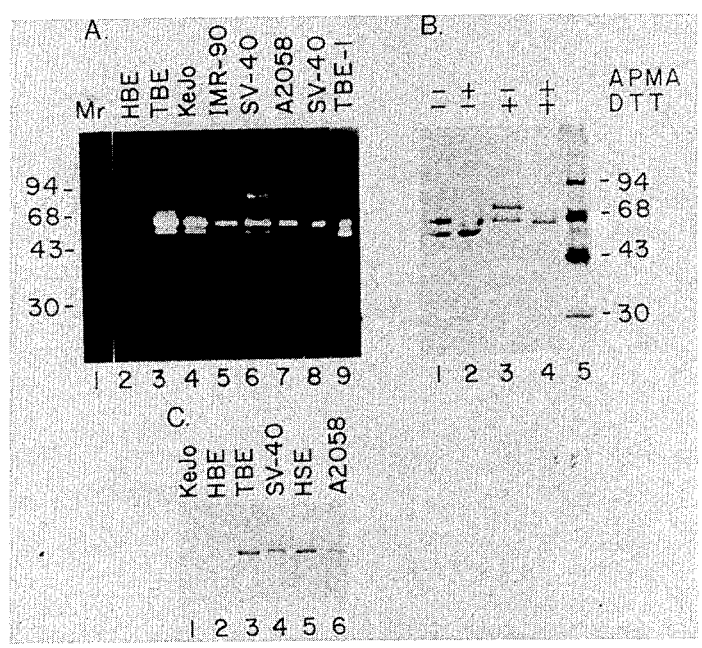

While the specification concludes with claims particularly pointing out and distinctly claiming the subject matter regarded as forming the present invention, it is believed that the invention will be better understood from the following detailed description of preferred embodiments of the invention taken in conjunction with the appended drawings, in which FIG. 1 shows three gel electrophoretic patterns in panels A, B, and C as follows:

A. This panel shows gelatin zymography of crude and purified 66 kDa type IV collagenase (gelatinase), unreduced. Samples of conditioned medium (100 μL) were dialyzed, lyophilized, and subjected to sodium dodecylsulfate polyacrylamide gel electrophoresis (NaDodSO$_4$-PAGE) without reduction. Human bronchial epitheial cells (HBE, lane 2), H-ras-transformed bronchial epithelial cells (TBE-1, lane 3), human skin fibroblasts (KeJo WU 80547, lane 4), fetal lung fibroblasts (IMR-90, lane 5), SV-40 transformed fetal lung fibroblasts (SV-40, lane 6), melanoma (A2058, lane 7). Purified 66 kDa SV-40 gelatinase (10 ng, lane 8) and purified TBE gelatinase (10 ng, lane 9) are shown for comparison. The zymogram was developed for 2 h. Lane 1 shows standard molecular weight ($M_r$) markers in kilodaltons (kDa).

B. This panel shows organomercurial activation of purified TBE-1 type IV procollagenase (gelatinase.) Samples of TBE-1 proenzyme were incubated with (+, lanes 2 and 4) or without (−, lanes 1 and 3) 0.5 mM APMA for 3 h at 37 C. Samples (2 μg) were subjected to NaDodSO$_4$-PAGE either with (+, lanes 3 and 4) or without (−, lanes 1 and 2) reduction with 10 mM dithiothreitol. The gel was stained with Coomassie Blue and the $M_r$ markers are shown for comparison.

C. This panel shows immunoblot analysis of 66 kDa type IV collagenase (gelatinase), unreduced, from the conditioned medium of several cell strains as designated in A. Samples (100 μl) were subjected to NaDodSO$_4$-PAGE, transferred to nitrocellulose and stained using TBE-1 type IV collagenase (gelatinase) antiserum. Lane 5 represents 50 ng of purified human skin explant gelatinase.

Figure 2:
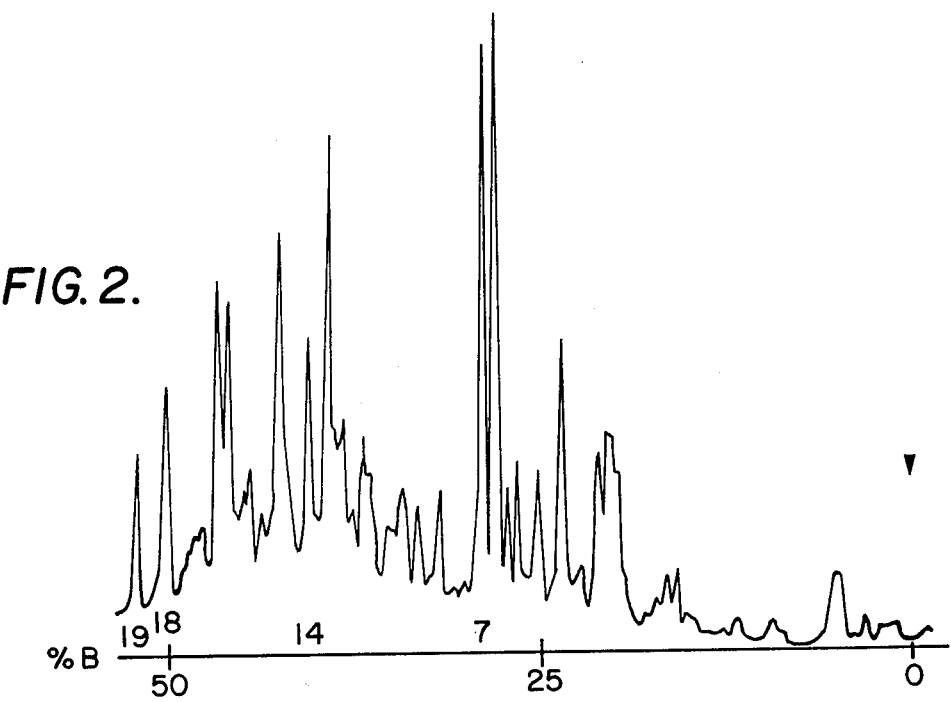

FIG. 2 shows a Microbore HPLC chromatogram of a tryptic digest of purified type IV collagenase (gelatinase). An enriched preparation of TBE-1 type IV collagenase (gelatinase) was separated on NaDodSO$_4$-PAGE, electroeluted from the gel, digested with trypsin and placed on an Applied Biosystems 130A Microbore 1×50 mm HPLC column equilibrated with 0.07% trifluoroacetic acid (TFA). The column was developed with a linear gradient of 0-70% acetonitrile at 1%/min. The numbered peaks were subjected to amino acid sequence analysis.

FIGS. 3A and 3B show the nucleotide sequence of human type IV collagenase (gelatinase) cDNA. The translated protein sequence of the enzyme is shown under the DNA sequence. The amino terminus of the mature proenzyme is indicated by a star. The 2733 bp cDNA of clone pGEL 186.2 is split into Panels A and B in FIG. 3.

Figure 4:
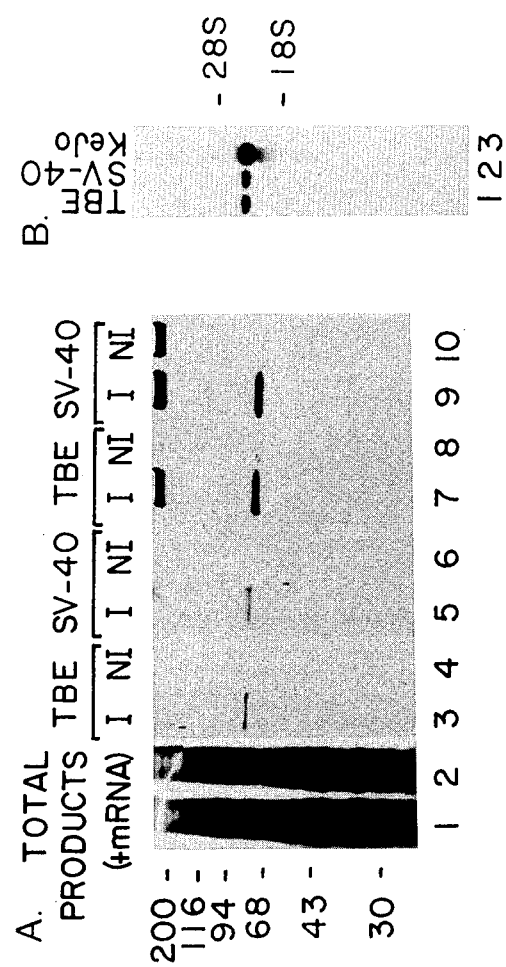

FIG. 4 shows the Cell-free Translation and Northern blot analysis of poly(A)+RNA in two panels A and B as follows:

A. Total ($^{35}$S)-methionine labeled in vitro translation products obtained with 1.0 μg of mRNA from TBE (lane 1), and SV-40 cells (lane 2), were immunoprecipitated using gelatinase specific (lanes 3 and 5) or non-immune antiserum (lanes 4 and 6). Type IV Procollagenase (progelatinase) immunoprecipated from the medium of $^{35}$S-labeled cultures of TBE-1 and SV-40 transformed cells is shown for comparison (lanes 7-10).

B. Northern Blot analysis of 5 μg of mRNA from TBE-1 (lane 1), SV-40 (lane 2), and KeJo (WU 80547) cells (lane 3).

Figure 5:
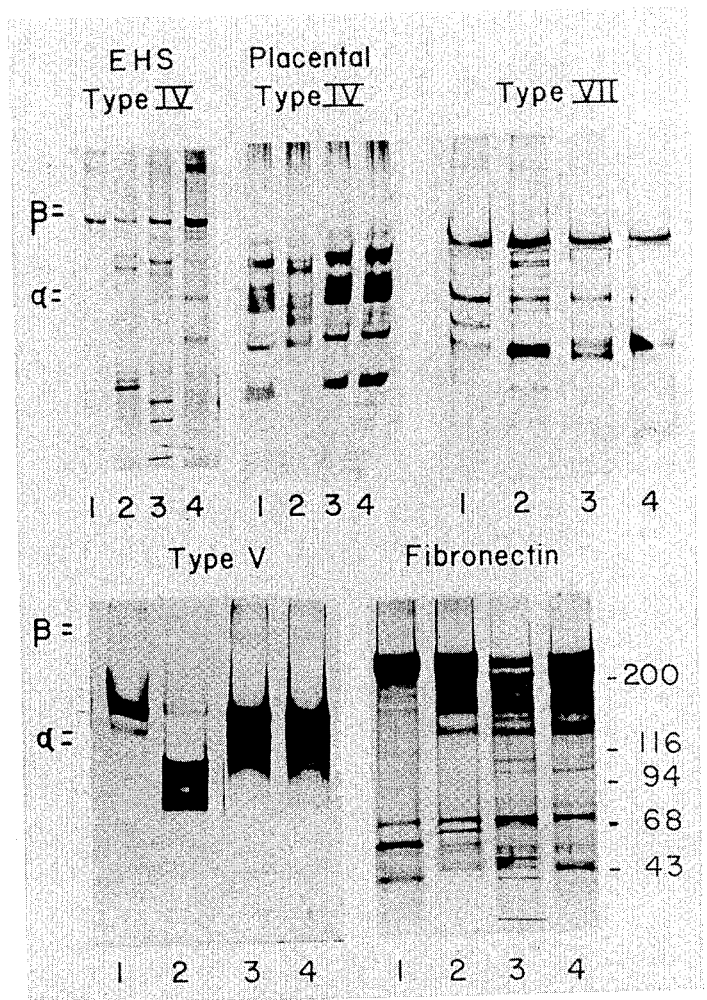

FIG. 5 shows by gel electrophoretic patterns the comparative analysis of the substrate specificity of type IV collagenase (gelatinase), stromelysin, and interstitial collagenase against collagen types IV, V, and VII and fibronectin. Collagen substrates (2 μg) were incubated at 32° C. for 8 h using an enzyme:substrate ratio of 1:10. Fibronectin (5 μg) was incubated for 8 h at 37° C. using an enzyme:substrate ratio of 1:50. Samples were reduced with dithiothreitol, electrophoresed in a 6% polyacrylamide gel and stained using silver. Control incubation with no enzyme (lanes 1), type IV collagenase (gelatinase) (lanes 2), stromelysin (lanes and collagenase (lanes 4). The positions of and α and β chains of type I collagen are shown for comparison.

FIG. 6 shows the protein sequence structural relationship of human type IV procollagenase (progelatinase) to interstitial human fibroblast procollagenase and prostromelysin and to rat prostromelysin (transin).

A. The top line represents the amino acid sequence of type IV procollagenase with amino acids numbered according to the sequence presented in FIG. 3. Second line—human interstitial procollagenase. Third line—human prostromelysin. Fourth line—rat transin. The line designated with + represents sequence of the part of the collagen binding domain of fibronectin homologous to domain II of type IV collagenase. In comparison the sequences corresponding to this domain are absent from three proteins and replaced with a star in this alignment.

B. Divergence of the primary structure of the 58 bp motif in the domain II of type IV collagenase. Each 58 amino acid long repeat is represented by a separate line with the first repeat being on top.

Figure 7:
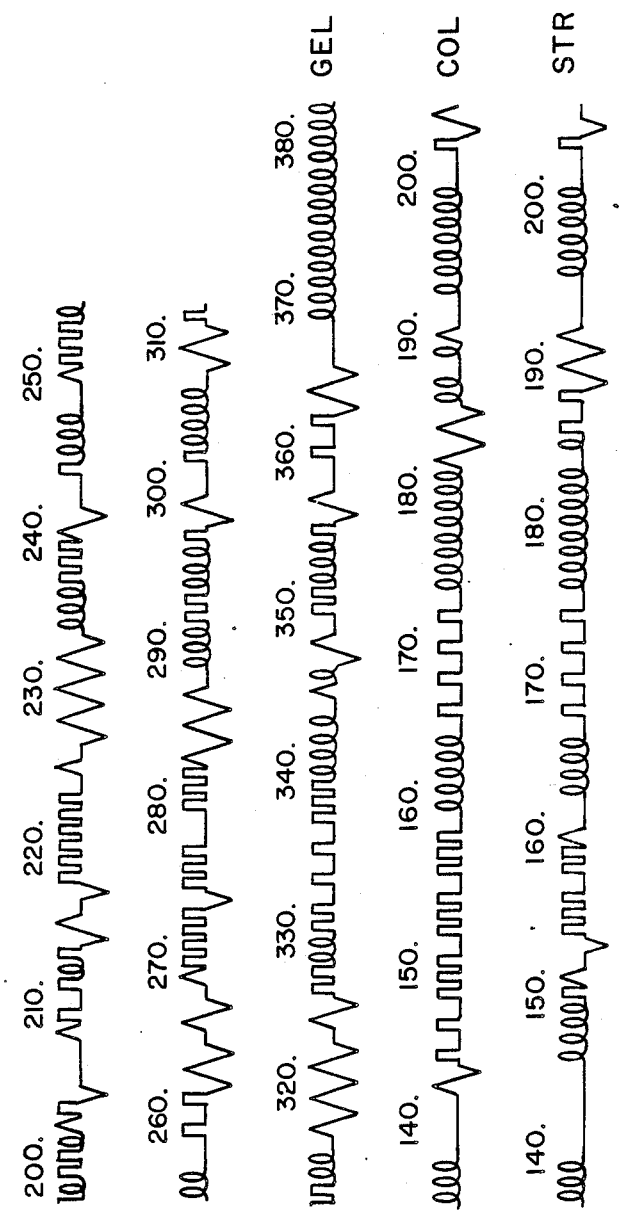

FIG. 7 is a schematic which shows a comparison of the secondary structure of human type IV procollagenase (progelatinase), procollagenase and prostromelysin. The secondary structure of the protein portion directly preceeding the zinc binding site is represented by a diagram generated according to the predictions of protein conformation of Chou and Fasman, 1978, infra. The sequences aligned 30 according to the position of the zinc binding sites and the extension toward the amino terminal ends are shown. The first, second, and third lines correspond to the 58 amino acid long motif of the type IV collagenase domain II. The fourth line—corresponding portion of the protein from interstitial collagenase (Goldberg, et al., 1986, infra) and the fifth line—stromelysin (Wilhelm, et al., 1987, supra).

FIG. 8 shows the restriction map (A) and nucleotide sequence of the type IV collagenase gene 5' proximal flanking region (B).

A. Restriction sites relevant to the plasmid construction are shown. Transcription (TS) and translation (AUG) start sites are indicated. The DraI site was used for subcloning the 3' endpoint of the probe used for S1 nuclease mapping.

B. Transcription start site (+1), cDNA start (*), three potentia Sp1 binding sites (boxed) and the upstream, out-of-frame ATG ( ) are indicated. The DraI and BssHII sites indicated in (A) are at map positions +10 and +260, respectively.

FIG. 9 shows the nucleotide sequence of the complete and expressible cDNA of the type IV collagenase in which a fragment of type IV collagenase genomic DNA and the cDNA clone of FIG. 3 were joined using synthetic DNA linker.

Standard biochemical nomenclature is used herein in which the nucleotide bases of DNA or oligonucleotides are designated as adenine (A); thymine (T); guanine (G); and cytosine (C). Amino acids are shown either by three letter or one letter abbreviations as follows:

| Abbreviated Designation | | Amino Acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Commonly available restriction endonucleases used herein have the following restriction sequences and (indicated by arrows) cleavage patterns.

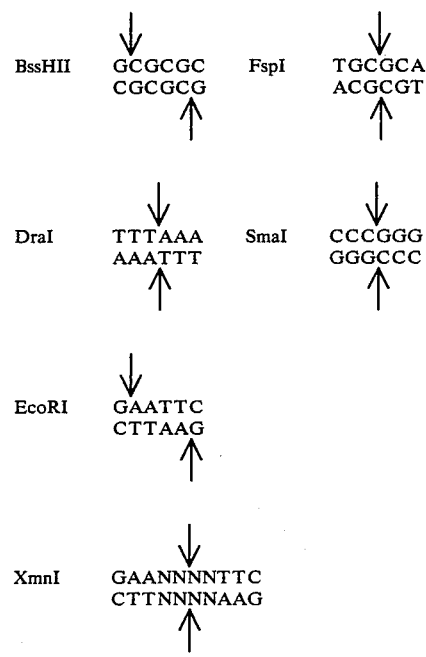

In order to illustrate specific preferred embodiments of the invention in greater detail, the following exemplary laboratory preparative work was carried out.

EXAMPLE 1

Materials and Methods

Cell lines used herein are also described by Wilhelm et al., Proc. Natl. Acad. Sci. USA, 84, 6725–6729 (1987). H-ras transformed human bronchial epithelial cells (TBE-1) were obtained from Dr. G. Yoakum (NIH). Cells were labeled, where indicated, by incubating with $^3$H-leucine at 20 ci/ml (154 Ci/mmol) in serum free, leucine free medium, or with 200 Ci/ml of $^3$H-mannose in low glucose medium.

All methods used, including oligonucleotide synthesis, in vitro translation, Northern and Western blot analysis, zymogram preparation, digestion with endoglycosidases F and H, construction of the human fibroblast cDNA library, and colonly screening, are conventional and were performed as described for human fibroblast collagenase by Wilhelm et al., Proc. Natl. Acad. Sci. USA 83, 3756–3760 (1986) and Goldberg et al., J. Biol. Chem. 261, 6600–6605 (1986); and stromelysin by Wilhelm et al., Proc. Natl. Acad. Sci. USA, 84, 6725–6729 (1987), without significant modifications.

Activation of progelatinase was performed using the organomercurial p-aminophenylmercuric acetate (APMA). A stock solution of 0.01 M APMA in 0.05 N NaOH was prepared immediately prior to use. Proenzyme samples were adjusted to 0.05 M Tris-HCl, pH 7.5, to avoid significant changes in pH upon addition of APMA. Progelatinase was incubated with a final APMA concentration of 0.5 mM for 3 hours at 37° C.

DNA sequences were confirmed on both strands using the partial chemical degradation method of Maxam and Gilbert, Methods Enzymol. 65, 499–560 (1980). In addition, about 60% of the sequence was confirmed using synthetic primers to "walk" along double stranded DNA and the dideoxynucleotide induced chain termination sequencing method of Sanger, Proc. Natl. Acad. Sci. USA 74, 5463–5467 (1977).

Monospecific antiserum was prepared as described by Wilhelm et al., Proc. Natl. Acad. Sci. USA 84, 6725–6729 (1987), using protein antigen incorporated in NaDodSO$_4$ gel slices emulsified with Freund's adjuvant.

Protein Sequencing. A partially purified preparation of gelatinase was subjected to NaDodSO$_4$PAGE gel electrophoresis and electroelution as described by Hunkapillar, Methods Enzymol. 91, 227–236 (1983). After electrodialysis the protein sample was removed from the cell and lyophilized in a Speed-Vac concentrator (Savant). The pellet was redissolved in 50 mM ammonium acetate and precipitated with 10 volumes of ethanol for 18 h at 20° C. The aminoterminal sequence was then determined on 10% of the sample material using an Applied Biosystems 470A gas phase sequencer with an on-line detection system. The rest of the sample was further purified by two consecutive precipitations with ethanol as above to remove the excess NaDodSO$_4$. Finally, the preparation was redissolved in 50 mM ammonium acetate and subjected to digestion with 5% (w/w) TPCK-treated (N-tosyl-L-phenylalanine chloromethyl ketone) trypsin in 100 μl total volume at room temperature for 18 h. The tryptic digest was acidified with trifluoroacetic (TFA) acid to a final concentration of 0.1% and applied on an Applied Biosystems 130A Microbore 1×50 mm HPLC column equilibrated with 0.07% TFA. The column was developed with a linear gradient of 0–70% acetonitrile in 0.07% TFA at 1%/min. Peaks were collected manually and subjected to amino acid sequence analysis as described above.

Purification of a 72 kDa gelatinolytic metalloprotease from H-Ras transformed bronchial epithelial cells (TBE-1). Conditioned serum-free culture medium (5 L) from TBE-1 cells was applied to a 2.5×10 cm zinc-chelate Sepharose® column equilibrated with 5 mM $CaCl_2$ in 20 mM Tris-HCl, pH 7.5 (Tris-$CaCl_2$ buffer) containing 150 mM NaCl, which was connected directly to a Reactive-Green Agarose affinity chromatography column equilibrated in the same buffer. The 72 kDa metalloprotease did not bind to the zinc-chelate column and was eluted from the Green column using a 0.15–1.5 M NaCl gradient (300 ml) in Tris-$CaCl_2$ buffer. The fractions were assayed for enzyme activity semi-quantitatively on gelatin zymograms, pooled, dialyzed against Tris-$CaCl_2$ buffer containing 0.01% Brij®-35 (polyethylene glycol fatty alcohol ether), and applied to a 1.0×5.0 cm column of heparin-agarose (Bio-Rad). The enzyme was eluted using a Tris-$CaCl_2$ buffer containing 0.1 M NaCl and 0.01% Brij and dialyzed against 5 mM Tris-HCl, pH 7.5, containing 0.1 mM $CaCl_2$ and 0.005% Brij. The sample was concentrated 40-fold using a Speed-Vac concentrator (Savant) and applied to a 0.5×60 cm column of ACA-44 equilibrated in Tris-$CaCl_2$ buffer containing 0.2 M NaCl and 0.01% Brij. The enzyme was dialyzed against Tris-$CaCl_2$ buffer containing 0.01% Brij and frozen at −70° C. The yield of purified enzyme was in the range of 50 μg per liter of culture medium. Alternatively, the 72 kDa metalloprotease could be purified using gelatin Sepharose (Sigma) as described by Hibbs et al., *J. Biol. Chem.* 260, 2493–2500 (1985). Briefly, the enzyme pool from the Green Agarose column was adjusted to 0.5 M NaCl and 0.01% Brij and applied to a 1.6×10 cm column of gelatin-Sepharose. The enzyme was eluted using 7.5% dimethylsulfoxide (DMSO) and dialyzed against Tris-$CaCl_2$ buffer containing 0.01% Brij.

Enzyme assays. Substrates used were guinea pig Type I-collagen or gelatin isolated as described previously by Stricklin et al., *Biochemistry* 16, 1607–1615 (1977) and Seltzer et al., *J. Biol. Chem.* 256, 4662–4668 (1981); pepsinized placental Type IV collagen; mouse EHS type IV collagen obtained from Collaborative Research and further purified by DEAE-Cellulose chromatography as described by Kleinman et al., *Biochemistry* 21, 6188–6193 (1982); placental types V and VII collagens; and purified mouse laminin and human plasma fibronectin obtained from BRL/Gibco Laboratories.

Gelatinolytic and collagenolytic activity were assayed as described by Stricklin et al., supra, and Wilhelm et al., *Proc. Natl. Acad. Sci.* 83, 3756–3760 (1986), using $^{14}C$-labeled guinea pig skin collagen (50,000 cpm/mg) except that assays contained 0.01% Brij. Assays using EHS or placental Type IV collagen and Types V and VII collagens as substrates (2–3 μg per assay) were performed at 32° C. using an enzyme:substrate ratio of 1:10 for 7–12 h in 25 μl reaction mix containing 50 mM Tris-HCl, pH 7.5, 150 mM NaCl, 5 mM $CaCl_2$, 0.01% Brij and 0.05 mM organo-mercurial APMA. Reactions were terminated by the addition of EDTA to a final concentration of 10 mM. Samples were reduced and electrophoresed on $NaDodSO_4$-polyacrylamide gels (6%) and stained with either Coomassie-Blue or silver [Merril et al., *Science* 211, 1437 (1981)].

The results of the above laboratory preparative work leading to the development of the complete primary structure, substrate specificities, and evidence for the identity of human skin fibroblast type IV collagenase (gelatinase) are shown in FIGS. 1 to 7 of the drawings and Tables I and II as further described in detail below.

Human Bronchial Epithelial Cells Secrete a Major ECM Metalloprotease in Response to Transformation with H-ras Oncogene. The inventors have also characterized human fibroblast collagenase [Stricklin et al., supra; Wilhelm et al., *Proc. Natl. Acad. Sci. USA* 83, 3756–3760 (1986); and Goldberg et al., supra;] and stromelysin [Wilhelm et al., *Proc. Natl. Acad. Sci. USA* 84, 6725–6729 (1987)], which are two major ECM metalloproteases secreted by a variety of normal and tumorigenic human cell strains. Using $NaDodSO_4$ polyacrylamide gels impregnated with substrate (zmyograms), the pattern of metalloprotease secretion was analyzed. Casein zymograms of human skin fibroblast conditioned media reveal four major bands of proteolytic activity; at 60 and 57 kDa (glycosylated and unmodified prostromelysin) and 55 and 52 kDa (glycosylated and unmodified procollagenase). As shown in FIG. 1 (lane 1) gelatin zymograms demonstrate a fifth major band of activity at 66 kDa. In addition, both casein (not shown) and gelatin zymograms of TBE-1 conditioned medium (FIG. 1, lane 2) show a single major band of proteolytic activity at 66 kDa (see below) co-migrating with that from skin fibroblast media, but absent from the media conditioned by untransformed human bronchial epithelial cells (FIG. 1, lane 3). The activity was completely inhibited by EDTA (not shown).

To characterize the gelatinolytic enzyme secreted by TBE-1 cells and establish its relationship to the metalloprotease of identical $M_r$ from other cell sources, a partial amino acid sequence was determined, and monospecific rabbit antiserum was raised. The TBE-1 conditioned media was partially purified on a reactive red column, lyophilized and subjected to $NaDodSO_4$-PAGE as described above. Gel slices containing the 66 kDa protein were emulsified with adjuvant and injected into rabbits. The remainder of the protein was electroeluted from the gel [Hunkapillar et al., *Methods Enzymol.* 91, 227–236 (1983)], precipitated with ethanol and digested with trypsin. The acidified trypsin digest was chromatographed on an Applied Biosystems Microbore HPLC 1×50 mm column (FIG. 2). Four of the peaks (Nos. 7, 14, 18, 19) along with an undigested sample, were subjected to amino acid sequence analysis. Amino acid sequences of the four peptides and of the 66 kDa protein amino terminus are presented in Table I.

TABLE I

| Peptide | Sequence |
| --- | --- |
| NP | APSPIIKFPGDVAPKTDKEL AVQYLNTFY |
| P14 | IIGYTPDLDPETVDDAFAR |
| P18 | DKPMGPLLVATFWPELPEK |
| P19 | LIADAWNAIPDNLDAVVDLE GGGHSYFFK |
| P7 | WEHGDGYPFDGK |

| Oligonucleotide | Sequence |
| --- | --- |
| ON93 | GA/GTAICCA/GTGT/CTCCC |
| ON36 | GCTCCAGTTAAAGGCGGCAT |

Table I represents the amino acid sequence of tryptic peptides of human type IV collagenase (gelatinase). In Table I, NP is the $NH_2$-terminal sequence of gelatinase from a non-trypsin treated sample. Tryptic peptides P14, P18, P19 and P7 correspond to the peaks presented in FIG. 2. ON93 represents the oligonucleotide probe synthesized from the amino acid sequence underlined (P7). In this oligonucleotide, I designates the nucleoside inosine. Oligonucleotide, ON36, was constructed to facilitate further screening of the complete cDNA as described below.

The results presented in FIG. 1C show that monospecific antiserum raised against the 66 kDa enzyme secreted by H-ras transformed TBE-1 cells recognizes the 66 kDa protease secreted by human fibroblasts derived from skin, lung and SV-40 transformed lung fibroblasts, as well as gelatinase purified from skin explants. The antibody was not able to recognize a major gelatinolytic activity band at 92 kDa secreted by SV40-transformed fibroblasts or by polymorphonuclear leukocytes after TPA induced protease release (data not shown). These observations lead to the conclusion that all examined cells were capable of secreting a gelatinolytic protease identical to that secreted by the TBE-1 cell line. To further support this conclusion, the amino acid sequence was determined for the 66 kDa enzyme secreted by SV40-transformed human lung fibroblasts in the fashion described for TBE-1 derived enzyme. The sequence was identical to the one presented in Table I. These data presented a sufficient justification for an attempt to isolate a cDNA clone representing gelatinase mRNA from a skin fibroblast cDNA library and to establish whether such a clone would contain coding information for all four peptides and the amino terminal sequence obtained from TBE-1 enzyme (Table I).

The underlined peptide sequence was translated and oligonucleotide probes were synthesized with the sequence presented in Table I. The probes were used to screen a cDNA library of human skin fibroblast mRNA as described earlier by Goldberg et al., supra, from which 22 gelatinase clones were isolated. The longest clone, pGel 186.2, contains 2733 bp and represents almost the full gelatinase mRNA sequence with the exception of the leader sequence and sequence coding for the first few amino acids of the signal peptide. Since pGel 186.2 cDNA was the longest among a significant number of clones, an oligonucleotide probe ON-36 (Table I) was constructed to facilitate further screening of the complete cDNA. Eight more clones were isolated and screened for the longest insertion between the vector end and Xmn 1 site positioned 131 bp from the 5' end of the pGel 186.2 DNA. All candidates were of identical length and no extension into the leader RNA sequence was found. Since both full length collagenase and stromelysin clones were obtained from the same library, and 30 gelatinase clones in total were screened for the presence of the leader sequence, it was concluded that a specific secondary structure of the gelatinase mRNA was able to block the reverse transcriptase advancement beyond the end point of pGel 186.2 and the other 8 clones of exactly the same length. The pGel 186.2 cDNA has been sequenced on both strands using the partial chemical degradation method of Maxam and Gilbert, supra. The sequence presented in FIG. 3 has coding capacity for the last 13 amino acids of the signal peptide and 631 amino acids of gelatinase protein followed by a 750 bp long 3' untranslated region, including a putative poly A addition site. The sequence of the mature enzyme amino terminus as shown in Table I, as well as all four peptides can be found in the defined protein sequence (FIG. 3). These data supported the conclusion that the gelatinolytic enzyme secreted by human bronchial epithelial cells after transformation with the H-ras oncogene is the same as one constitutively secreted by normal human skin fibroblasts and all liklihood identical to the 66 kKa gelatinase obtained from sourced presented in FIG. 1 and recognized by antigelatinase antibody.

Gelatinase is capable of initiation of degradation of basement membrane components in vitro. Frequently, the gelatin zymogram of some samples of TBE-1 metalloprotease revealed a doublet of gelatinolytic activity at 66 and 62 kDa (unreduced) on $NaDodSO_4$-PAGE (FIG. 1A, lanes 8,9), consistent with the presence of two protein bands in the purified enzyme preparation (FIG. 1B, lane 1). Reduction with dithiothreitol resulted in an increase in the apparent $M_r$ of both polypeptides to 72 and 66 kDa (FIG. 1B, lane 3). Treatment with the organomercurial, APMA, resulted in the conversion of the 72 kDa proenzyme species into a single activated enzyme form of 66 kDa (reduced, FIG. 1B, lane 4) or 62 kDa (unreduced, FIG. 1B, lane 2). Unlike its action on procollagenase and prostromelysin, trypsin failed to convert the 72 kDa progelatinase into an activated 66 kDa enzyme species (data not shown).

In vitro cell-free translation (FIG. 4A) of mRNA from TBE-1 and SV-40-transformed fetal lung fibroblast revealed a single major immunoprecipitable translation product of 78 kDa consistent with the presence of an uncleaved signal peptide. Northern blot analysis (FIG. 4B) of poly A+RNA from TBE-1 cells (lane 1), SV-40 fetal lung fibroblasts (lane 2), and normal skin fibroblasts [KeJo(WU 80567), lane 3] revealed a single mRNA band of 3.1 kb which hybridized to the gelatinase cDNA clone pGel 186.2. The inventors previously reported that the minor, higher molecular weight proenzyme species encoding collagenase and stromelysin contains N-linked oligosaccharide(s) [Wilhelm et al., Proc. Natl. Acad. Sci. 83, 3756–3760 (1986); Wilhelm et al., Ibid. 84. 6725–6729 (1987)]. In contrast to these two metalloproteases, gelatinase does not contain N-linked oligosaccharides as demonstrated by the use of tunicamycin and treatment with endoglycosidases F and H (data not shown). Although two potential N-linked glycosylation sites were found in the predicted gelatinase primary structure at Asn-546 and Asn-613, the conserved site in both collagenase and stromelysin at Asn-120 is absent in gelatinase. Taken together, these observations indicate that the presence of lower molecular weight gelatinase on zymograms and in purified preparations (FIG. 1A) is due to a partial activation of the enzyme concomitant with the loss of 6 kDa in molecular weight. Treatment with the organomercurial APMA, induces the complete activation of the proenzyme and its conversion to lower $M_r$ species. Analogous consequences of the APMA action have been observed with collagenase and stromelysin.

To establish the range of substrate specificity of the gelatinase from TBE-1 cells and compare it with collagenase and stromelysin, a number of ECM proteins were subjected to proteolysis with each of the three purified enzymes. (Table I). The final specific activity of gelatinase against $^{14}C$-gelatin was 1600 units/mg of protein which is similar to that reported for human skin explant gelatinase and PMN gelatinase. Although the enzyme had no, or low, activity against type I collagen, proteoglycans, and laminin, it was capable of degrading both murine EHS and human placental type IV collagen, types V and VII collagens, and fibronectin. Gelatinase also degrades type V collagen, producing degradation fragments of approximately 90 and 70 kDa (Table II). Human polymorphoneuclear leukocyte and rabbit bone gelatinase have also been reported to degrade native type V collagen [Murphy et al., *Biochim. Biophys Acta* 831, 49–58 (1985); Hibbs et al., *J. Biol. Chem.* 260, 2493–2500 (1985)]. Gelatinase exhibits a low level of activity against fibronectin in comparison to stromelysin and collagenase.

As shown in FIG. 5, upon incubation of EHS type IV collagen at 32° C. with gelatinase from TBE-1 cells produces degradation products of 140 and 125 kDa as determined by NaDodSO$_4$-PAGE. These products were distinct from those produced by purified fibroblast stromelysin (FIG. 5, lane 3) of 165, 130, 120, 95, and 55 kDa. Interstitial fibroblast collagenase also exhibited some activity on this substrate, as demonstrated by cleavage products of 165, 130, 95 and 70 kDa in size (FIG. 5, lane 4) which are similar to those produced by pepsin [Tryggvason et al., *Biochemistry* 19, 1284–1289 (1980)]. In contrast, only gelatinase was capable of degrading pepsinized placental type IV collagen, resulting in degradation products approximately 10 kDa lower in molecular weight and similar to those reported for rabbit bone gelatinase by Murphy et al., supra.

The foregoing data clearly indicate that each of the three metalloproteases is capable of proteolytic degradation of a range of ECM proteins with an overlap in substrate specificity. It is of interest that both stromelysin and gelatinase showed significant activity against structural macromolecules of the basement membrane. Since TBE-1 cells do not express stromelysin, and zymogram analysis failed to reveal the secretion of metalloproteases other than gelatinase, an attempt was made to establish the presence of additional enzyme(s) capable of degrading basement membrane proteins, in particular, type IV collagen. Crude conditioned medium from TBE-1 cells was passed over a Sepharose TIMP (tissue inhibitor of metalloprotease) antibody column. The inhibitor-depleted medium was applied either to a 1 ml column of gelatin Sepharose or Sepharose coupled to EHS-type IV collagen. The gelatin column was eluted as described above and the type IV column was eluted using 1 M NaCl and 50% ethylene glycol, as previously described by Salo et al., *J. Biol. Chem.* 258, 3058–3063 (1983). Gelatin zymograms, gelatinase and type IV collagenase assays demonstrated that: (1) gelatinolytic and type IV collagenolytic activity bound quantitatively to gelatin; (2) no detectable type IV activity was present in the fall through from the gelatin Sepharose column; (3) approximately 10% of the 72 kDa gelatinase bound to and was eluted from the type IV column. This fraction did not exhibit preferential activity for type IV collagen relative to gelatin. Based on these observations, it was concluded that the 72 kDa gelatinase represents a single enzyme, secreted by TBE-1 cells, capable of degrading type IV collagen. In addition, because of its ability to cleave both native and pepsinized type IV collagen, the 72 kDa gelatinolytic protease will now be referred to as type IV collagenase.

Type IV Collagenase (Gelatinase) is Structurally Related to Fibroblast Collagenase and Stromelysin and Carries an Additional 175 Amino Acid-Long Domain Homologous to the Collagen Binding Domain of Fibronectin. The results show that purified gelatinase secreted by TBE-1 cells is capable of initiating degradation of ECM macromolecules including types IV, V, and VII collagens and fibronectin. The substrate specificities of type IV collagenase (gelatinase), fibroblast collagenase and stromelysin show a degree of overlap when native ECM components are subjected to proteolysis. Fibroblast collagenase is capable of proteolysis of Gly-Leu and Gly-Ile peptide bonds in gelatin obtained from denatured types I-V collagen [Welgus et al., *J. Biol. Chem.* 257, 11534–11539 (1982)]. Stromelysin digests Gly-Ile bonds present in synthetic peptides [Galloway et al., *Biochem. J.* 209, 741–752 (1983)]. At present, it is not known whether the Gly-Leu peptide bond is a substrate for stromelysin, since the synthetic peptides used did not contain this sequence. Type IV collagenase (gelatinase) isolated from skin explants degrades gelatin with cleavage of both Gly-Leu and Gly-Ile bonds [Seltzer et al., *J. Biol. Chem.* 256, 4662–4668 (1981)]. All three enzymes are secreted metalloproteases requiring intrinsic Zn++ [Seltzer et al., *Biochim. Biophys. Acta* 485, 179–187 (1977)] and extrinsic Ca++ for activity [Seltzer, *Arch. Biochem. Biophys* 173, 355–361 (1976)].

The alignment presented in FIG. 6 shows that all three human enzymes and rat stromelysin are structurally related. The overall homology shows that fibroblast collagenase and human and rat stromelysin are more closely related to each other than to human type IV collagenase (gelatinase). The homology divides gelatinase into three domains. The amino terminal domain, I, of 192 amino acids is well-conserved in all presented proteins. The carboxyl end domain, III, of 264 amino acids, is conserved less well than domain I, but is clearly aligned in all four proteins. Domain II consists of a 58 amino acid long motif repeated three times in head-to-tail configuration. This 175 amino acid insertion constitutes a new entity in the protein sequence of the enzyme family and has no significant homology to either of the two domains shared among the proteases.

The divergence of protein sequences among these three motifs is shown in FIG. 6. The third 58 amino acid repeat in gelatinase is positioned directly in front of the well conserved and shared sequence of the putative zinc binding site (residues 368–385) [McKerrow, *J. Biol. Chem.* 262, 5943 (1987)]. By implication, this sequence may be involved in the formation of the enzyme's active center. Since no sequence homology between the third repeat and the sequence preceding the zinc binding site of the other presented enzymes can be found, no comparison was made of the predicted secondary structures of the proteins in the areas under question. FIG. 7 shows a representation of the secondary structure prediction based on the prediction of protein conformation by Chou and Fasman, *Ann. Rev. Biochem.* 47, 251–276 (1978). The first three lines represent the predicted secondary structure of the domain II repeats aligned as in FIG. 6 with the extruding part corresponding to the sequence of the zinc binding site. The fourth and fifth lines represent the predicted secondary structure of collagenase and human stromelysin correspondingly anchored in position by the conserved sequence of the zinc binding site. The alignment shows the zinc binding site of all three enzymes situated within the α-helical region of the protein. Most interestingly, the divergence of the repeats in domain II is evidently directed in a way that leads to convervation of the secondary structure features of the protein immediately adjacent to the zinc binding site, despite the absence of sequence homology in this region. Indeed, a development of two well separated α-helical regions followed by a probable β-sheet structure adjacent to the zinc binding site can be seen as one moves along the gelatinase protein from the first to the third repeat of the second domain. The most intriguing observation is that repeats of domain II are closely related to the type II motif of the collagen binding domain of fibronectin as shown in the alignment of FIG. 6. It is most likely, therefore, that the ability of type IV procollagenase (progelatinase) to bind to immobilized gelatin can be explained by the presence of domain II sequences.

TABLE II

| SUBSTRATES | 72-kDa TBE Gelatinase | Stromelysin | Collagenase |
| --- | --- | --- | --- |
| Type I collagen | — | — | 900 U/mg |
| Gelatin (Type I) | 1600 U/mg | 125 U/mg | 50 U/mg |
| Proteoglycan | .02/μg/min/μg | .6/μg/min/μg | .12 μg/min/μg |
| Fibronectin | + | ++ | ++ |
| Laminin | — | + | — |
| Type IV-EHS* | +++(.5/μg/h/μg) | +++(.5/μg/h/μg) | +(.1/μg/h/μg) |
| Type IV-placenta* | +++(.5/μg/h/μg) | — | — |
| Type V* | +++(1.0/μg/h/μg) | +(.1/μg/h/μg) | +.1/μ/h/μg) |
| Type VII* | + | + | + |

* = assays were performed at 32° C.
1 unit (U) = 1 g of substrates degraded/min under these conditions.

EXAMPLE 2

Expression of the Type IV Collagenase

To complete the structure of type IV collagenase mRNA, the type IV collagenase gene was isolated from a human placental DNA genomic library described for the human interstitial collagenase gene by Collier et al., *J. Biol. Chem.* 263, 10711–10713 (1988). The DNA of the genomic clones was subjected to Southern blot analysis (data not shown) using a 20 bp oligonucleotide complementary to the first 20 bp of cDNA sequence. A 2.8 kbp hybridizable Xmn-Xmn restriction fragment (FIG. 8A) spanning the 5' end of type IV collagenase gene was subcloned into bluescript-SK plasmid vector (Strategene). The transcription start site was mapped by S1 nuclease protection analysis, using a 1280 bp single stranded probe whose 3' terminus was 25 bp upstream of the cDNA 5' end (FIG. 8A and 8B). The major protected product migrated at 260 nucleotides, which positions the type IV collagenase transcription start site 285 bp upstream from the cDNA start as indicated in FIG. 8B. The sequence presented in FIG. 8B contains 290 bp upstream of the transcription initiation site, 237 bp of the 5' untranslated region, the initiating methionine codon (position +237; a second in-frame ATG is found 12 bp downstream; since the existing data do not allow for distinguishing which of these is the initiating methionine, the first ATG was arbitrarily chosen), sequence coding for 29 amino acids of the signal peptide and the first 29 amino acids of the proenzyme, overlapping with the sequence of the type IV collagenase cDNA clone (Example 1, FIG. 3A and 3B). The sequence of the 5' flanking region presented in FIG. 8B has some notable features. No TATA box can be found upstream of the start site; such TATA-less promoters have been described in several other genes [Dynan, *Trends Genet.*, pp. 196–198, Aug. 1986]. The sequence contains several potential SP1 binding sites (Dynan, Ibid.) within 120 bp upstream of the start site. The 5' untranslated region is highly GC rich and contains an upstream out-of-frame AUG (position +83). In these respects, this region is structurally similar to the 5' untranslated region of c-sis mRNA, [Rao et al., *Mol. Cell Biol.* 8. 248–256 (1988)], which is a potent translational inhibitor.

To reconstruct the complete and "expressible" cDNA gene of type IV collagenase, the fragment of type IV collagenase genomic DNA and the cDNA clone presented in FIG. 3 were joined using synthetic DNA linker.

Linker assembly. Six oligonucleotides (sequence shown below) were synthesized and kinased to introduce a 5' phosphate where indicated. Each pair of the oligonucleotides was annealed separately to make three double stranded fragments with complementary overhanging ends. The linker was then assembled by ligation of the annealed mixture of the three synthetic double stranded DNA fragments. The resulting product was isolated after electrophoresis on 12% acrylamide gel.

The plasmid p9.1BT, containing the genomic Xmn-Xmn fragment from the promoter area extending into the second intron of the gene, was digested with the restriction endonucleases FspI and BssHII. The resulting FspI BssHII fragment was isolated after electrophoresis on 1% agarose gel.

The type IV collagenase cDNA clone was digested with Xmn and SmaI and isolated from a 1% agarose gel.

The resulting precursors, the synthetic linker, the FspI BssHII genomic fragment, and the Xmn SmaI digested type IV collagenase cDNA clone were mixed and ligated to generate a recombinant clone. This recombinant clone contains the insert coding for the complete type IV collagenase RNA. The sequence of this clone presented in FIG. 9 was confirmed using the dideoxy chain termination sequencing method.

```
    CGCGCTCACGGGTCCCCTGAGGGCGCTCTGTCTCCTGGGCTGCCTG
       GAGTGCCCAGGGGACTCCCGCGAGACAGAGGACCCGACGGACGACTCGGTGC*P

P*CTGAGCCACGCCGCCGCCGCGCCGTCGCCCATCATCAAGTTCCCCG
       GGCGGCGGCGCGGCAGCGGGTAGTAGTTCAAGGGGCCGCTACAGC*P

P*GCGATGTCGCCCCCAAAACGGACAAAGAGTTGGCAGTGCAATACCTGAACA
       GGGGGTTTTGCCTGTTTCTCAACCGTCACGTTATGGACTTGT
```

Various other examples will be apparent to the person skilled in the art after reading the present disclosure without departing from the spirit and scope of the invention. It is intended that all such further examples be included within the scope of the appended claims.

What is claimed is:

1. The cDNA of human type IV collagenase (gelatinase) having the nucleotide sequence shown in FIGS. 3A and 3B of the drawings.

2. Human type IV collagenase (gelatinase) having the amino acid sequence as shown in FIG. 3 of the drawings.

3. The complete and expressible cDNA of human type IV collagenase having the nucleotide sequence as shown in FIG. 9 of the drawings.

4. Human type IV collagenase cDNA clone pGEL 186.2 containing a 2733 basepair insert having the nucleotide sequence shown in FIGS. 3A and 3B of the drawings.

5. A human type IV collagenase cDNA clone containing a 3020 basepair insert having the nucleotide sequence shown in FIG. 9 of the drawings.

* * * * *